(12) United States Patent
Bejan et al.

(10) Patent No.: US 7,049,399 B2
(45) Date of Patent: May 23, 2006

(54) PROCESS FOR THE PREPARATION OF POLYPEPTIDE 1

(75) Inventors: Elena Bejan, Brantford (CA); Gamini Weeratunga, Brantford (CA); Stephen E. Horne, Burlington (CA)

(73) Assignee: Apotex Pharmachem Inc., Brantford (CA)

( * ) Notice: Subject to any disclaimer, the term of this patent is extended or adjusted under 35 U.S.C. 154(b) by 517 days.

(21) Appl. No.: 10/326,994

(22) Filed: Dec. 24, 2002

(65) Prior Publication Data

US 2004/0091956 A1     May 13, 2004

(30) Foreign Application Priority Data

Nov. 13, 2002    (CA) .................................... 2411786

(51) Int. Cl.
*C07K 1/00* (2006.01)
*C07K 2/00* (2006.01)

(52) U.S. Cl. ............ 530/333; 530/337; 530/336; 530/335; 530/300; 530/350; 530/344

(58) Field of Classification Search ............... None
See application file for complete search history.

(56) References Cited

U.S. PATENT DOCUMENTS

| | | | |
|---|---|---|---|
| 3,849,550 A | 11/1974 | Teitelbaum et al. | 424/78 |
| 5,800,808 A | 9/1998 | Konfino et al. | 424/78.08 |
| 5,981,589 A | 11/1999 | Konfino et al. | 514/561 |
| 6,048,898 A | 4/2000 | Konfino et al. | 514/561 |
| 6,054,430 A | 4/2000 | Konfino et al. | 514/12 |

FOREIGN PATENT DOCUMENTS

| | | |
|---|---|---|
| WO | WO 95/31990 | 11/1995 |
| WO | WO 00/27417 | 5/2000 |

OTHER PUBLICATIONS

Teitelbaum, D. et al., "Suppression of Experimental Allergic Encephalomyelitis by a Synthetic Polypeptide", *Eur. J. Immunol.*, (1971), 1:242-248.

*Primary Examiner*—Bruce R. Campell
*Assistant Examiner*—Andrew D. Kosar
(74) *Attorney, Agent, or Firm*—Ivor M. Hughes; Marcelo K. Sarkis; Kitt Sinden

(57) ABSTRACT

A process for the preparation of a polypeptide designated in the present invention as 1, composed of the following amino acid units in the structure, namely: L-alanine, L-glutamic acid, L-lysine and L-tyrosine randomly arranged in the polypeptide 1, or pharmaceutically acceptable salts thereof, comprising the steps of:

(a) polymerization of a mixture of the N-carboxyanhydrides of L-alanine, L-tyrosine, a protected L-glutamate and a protected L-lysine to obtain protected copolymer 6 or salt thereof;

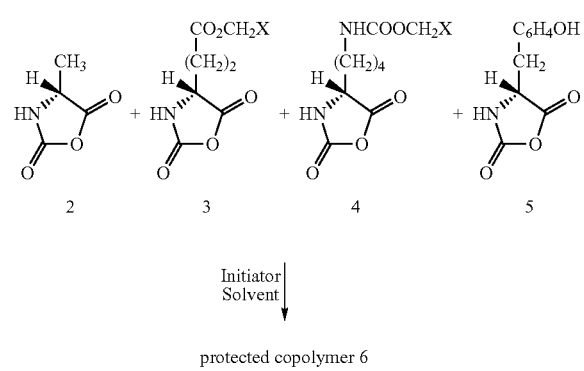

(b) deprotection of the protected copolymer 6 (or salt thereof) to produce polypeptide 1 or a pharmaceutically acceptable salt thereof in one single step;

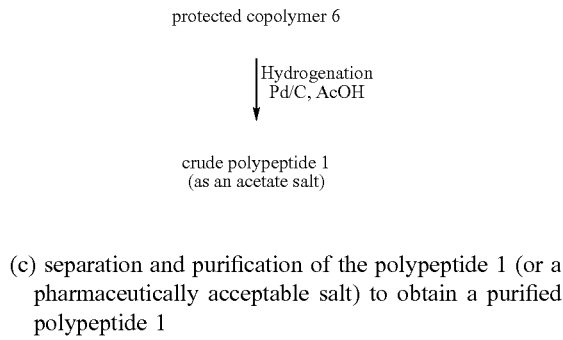

(c) separation and purification of the polypeptide 1 (or a pharmaceutically acceptable salt) to obtain a purified polypeptide 1

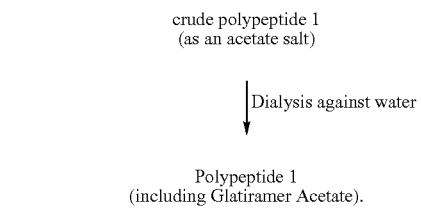

45 Claims, No Drawings

PROCESS FOR THE PREPARATION OF POLYPEPTIDE 1

Process for the preparation of polypeptide 1.

FIELD OF INVENTION

The present invention refers to a new process for the synthesis of polypeptide 1 and novel intermediates useful in the synthesis thereof.

BACKGROUND OF THE INVENTION

The present invention refers to a new process for the synthesis of polypeptide 1, comprising the following amino acid units in the structure, namely: L-alanine, L-glutamic acid, L-lysine and L-tyrosine randomly arranged in the polypeptide 1; of which Glatiramer Acetate is a representative example.

Glatiramer Acetate is a synthetic polypeptide analog of myelin basic protein (MBP), which is a natural component of the myelin sheath. It is also defined in the Physicians' Desk Reference, 56th Edition 2002 as consisting of acetate salts of synthetic polypeptides, containing four naturally occurring amino acids: namely, L-glutamic acid, L-alanine, L-tyrosine and L-lysine with an average molar fraction of 0.141, 0.427, 0.095 and 0.338 respectively. The average molecular weight is 4,700–11,000 daltons.

Interest in Glatiramer Acetate as an immunotherapy agent for multiple sclerosis stems from the 1950's observations that myelin components such as MBP prevent or arrest experimental allergic encephalomyelitis, a disease resembling multiple sclerosis (U.S. Pat. No. 3,849,550). Recently, it has been shown that Glatiramer Acetate is a novel, safe and effective treatment for patients with the exacerbating-remitting form of multiple sclerosis and it is the active ingredient of Copaxone™, a medicament used for the treatment of multiple sclerosis.

The process for the preparation of Glatiramer Acetate has been described in U.S. Pat. Nos. 6,048,898; 5,800,808; 5,981,589 and 3,849,550. They all employ as starting materials four N-carboxyanhydrides derived from alanine, γ-benzyl glutamate, N[ε]-trifluoroacetyl lysine and tyrosine. These monomers of N-carboxyanhydrides were prepared as described in the literature by the phosgene method shown in Scheme 1.

Scheme 1

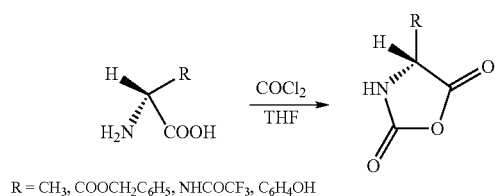

R = CH₃, COOCH₂C₆H₅, NHCOCF₃, C₆H₄OH

The process for the synthesis of Glatiramer Acetate is based on the polymerization of N-carboxyanhydrides of alanine 2, γ-benzyl glutamate 3, N[ε]-trifluoroacetyl lysine 7 and tyrosine 5, in anhydrous and cancer suspect solvent dioxane at room temperature for 24 hours using diethylamine as initiator (Scheme 2).

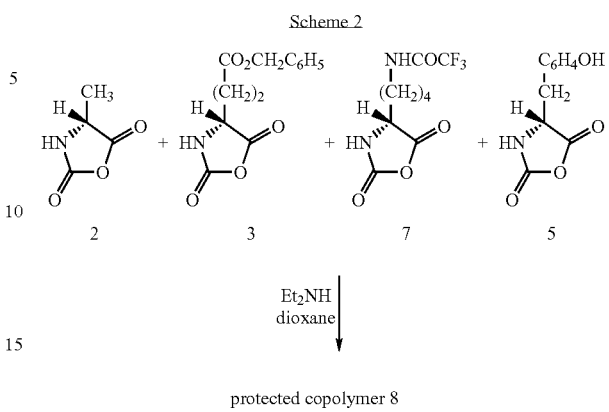

The deblocking of γ-benzyl groups (first deprotection) is effected by stirring the protected copolymer 8 in hydrobromic acid/acetic acid at room temperature for 17 hours. These conditions also facilitate the cleavage of the polypeptide thereby furnishing the intermediate 9.

The next step in the prior art literature process is the removal of N[ε]-trifluoroacetyl groups (second deprotection) of intermediate 9 by treatment with 1 M piperidine. In the final steps, Glatiramer Acetate is obtained by purification of intermediate 10 through dialysis, followed by treatment with acetic acid to form the acetate salt and by another purification by dialysis against water (Scheme 3).

Thus, the prior art literature procedure involves the polymerization of four N-carboxyanhydrides, two deprotection steps of intermediates 8 and 9 and two purification steps (Step 3 and 5 in Scheme 3) and one acetate salt formation step (Step 4 in Scheme 3).

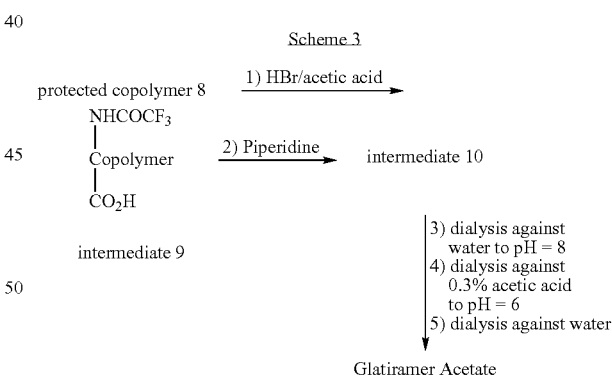

Glatiramer acetate with the required average molecular weight (4.7 to 11 kDa) can be obtained either by chromatography of intermediate 10 containing high molecular weight species and collecting the fractions without the undesired species or by partial acid or enzymatic hydrolysis to remove the high molecular weight species with subsequent purification by dialysis or ultrafiltration. Further methods to obtain Glatiramer Acetate having the required average molecular weight are based on the preparation of the desired species while the amino acids are still protected, followed by deprotection.

SUMMARY OF THE INVENTION

An object of the present invention is to provide a new and improved process for the synthesis of polypeptide 1. This process provides a three-step procedure for the synthesis of polypeptide 1 relative to the prior art.

More specifically, the present invention is directed to a new process for the preparation of a polypeptide designated in the present invention as 1 comprising the following amino acid units in the structure, namely: L-alanine, L-glutamic acid, L-lysine and L-tyrosine randomly arranged in the polypeptide 1, or a pharmaceutically acceptable salt thereof wherein said process, comprises the steps of:

(a) polymerization of a mixture of the N-carboxyanhydrides of L-alanine, L-tyrosine, a protected L-glutamate, and a protected L-lysine, to obtain protected copolymer 6 or a salt thereof;

(b) deprotection of the protected copolymer 6 or a salt thereof to afford polypeptide 1 or a pharmaceutically acceptable salt thereof in one single step;

(c) separation and purification of the polypeptide 1 or a pharmaceutically acceptable salt thereof.

The advantages of the current process are the result of (i) the novel choice of side chain protection on the glutamic acid and lysine moieties and (ii) the utilization of acetic acid as solvent for the deprotection step thereby permitting the isolation of polypeptide 1 as an acetate salt directly from the reaction mixture without any additional procedures. This results in advantages such as simplicity and minimized number of steps, a cost-effective process and an optimization of the productivity by carrying out more than one synthetic transformation in one step.

The new and improved process, according to the present invention, is also based on the polymerization of four N-carboxyanhydrides to prepare a new to protected copolymer 6 but the deprotection is achieved in one step due to the selection of the protecting groups in one instance, benzylic and carbobenzyloxy groups present on the glutamic acid and lysine units of the protected copolymer 6. The second step in the process is the deprotection of protected copolymer 6 said deprotection step is selected from the group consisting of: (i) catalytic hydrogenation under hydrogen pressure and (ii) catalytic transfer hydrogenation (CTH) preferably in acetic acid. More preferably, the catalysts are selected from the group consisting of Pd/C, Pd(OH)$_2$, and the like. In a preferred embodiment, the polypeptide 1 (as an acetate salt) is isolated directly from the reaction mixture after a single dialysis step.

According to one aspect of the invention, there is provided a process for the preparation of a polypeptide designated in the present invention as polypeptide 1, comprising the following amino acid units in the structure, namely: L-alanine, L-glutamic acid, L-lysine and L-tyrosine randomly arranged in the polypeptide 1, or a pharmaceutically acceptable salt thereof wherein said process comprises the steps of:

(a) polymerization of a mixture of the N-carboxyanhydrides of L-alanine, L-tyrosine, protected L-glutamate, and protected L-lysine, to obtain protected copolymer 6 or a salt thereof;

(b) deprotection of the protected copolymer 6 or a salt thereof to afford polypeptide 1 or a pharmaceutically acceptable salt thereof in substantially a single step;

(c) separation and purification of the polypeptide 1 or a pharmaceutically acceptable salt thereof, preferably, said polymerization is carried out at a temperature ranging between about 0 to about 80° C., and preferably said process further comprises a solvent. Said solvent is preferably selected from the group consisting of DMF, DMSO, CH$_2$Cl$_2$, dioxane or mixtures thereof.

In another aspect of the invention, said polymerization is carried out in the presence of an initiator, preferably said initiator comprises at least one of the following: diethylamine, triethylamine and diisopropylamine.

According to yet another embodiment of the invention, there is provided a process of manufacturing Glatiramer Acetate comprising a single step deprotection of a protected copolymer 6, said protected copolymer 6 comprising a mixture of L-alanine, L-tyrosine, a protected L-glutamate and a protected L-lysine, protected by at least one protecting group, preferably said at least one protecting group is selected from a substituted or unsubstituted γ-benzyl group or a substituted or unsubstituted N$^\epsilon$-benzyloxycarbonyl group or an aryl group, preferably said substituted γ-benzyl group or N$^\epsilon$-benzyloxycarbonyl group is substituted with at least one of the following: Br, Cl, NO$_2$, OCH$_3$.

Preferably, the deprotection step is selected from the group consisting of:

(i) catalytic transfer hydrogenation; and (ii) catalytic hydrogenation under hydrogen pressure.

In another aspect of the invention, said separation and purification of the polypeptide 1 is carried out in a single step, preferably said single step involves a single dialysis against water.

Preferably, said deprotection step is carried out in acetic acid, and preferably, said deprotection step is carried out at a temperature in the range of about 50 to about 80° C., and preferably, said deprotection step is carried out in the presence of a catalyst, preferably said catalyst is selected from Pd/C and Pd(OH)$_2$, and preferably, carried out at a pressure in the range of about 40 to about 100 psi.

Preferably, said catalytic transfer hydrogenation is carried out in the presence of acetic acid, and preferably, at a temperature in the range of about 50 to about 80° C., and preferably carried out under hydrogen pressure of about 40 to about 100 psi.

According to another aspect of the invention, said process further comprises at least one reagent selected from the group consisting of: formic acid, sodium formate, trialkyl ammonium formates, hydrazine, 1,3-cyclohexadiene, 1,4-cyclohexadiene, cyclohexene, and ammonium formate or mixtures thereof.

According to another aspect of the invention, the process of manufacturing Glatiramer Acetate further comprises subsequent separation and purification of Glatiramer Acetate, preferably said separation and purification of the Glatiramer Acetate is carried out in a single step, preferably said single step involves a single dialysis against water.

According to yet another aspect of the invention, the polypeptide 1 has an average molecular weight between 4,700 and 11,000 Da.

According to yet another aspect of the invention, said Glatiramer Acetate has an average molecular weight between 4,700 and 11,000 Da.

According to yet another aspect of the invention, there is provided a protected L-lysine is a protected, substituted N$^\epsilon$-Benzyloxycarbonyl L-lysine of formula 11:

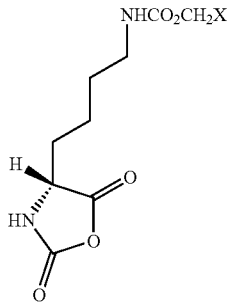

where X=$C_6H_5$, $C_6H_4Br$, $C_6H_4Cl$, $C_6H_4NO_2$ $C_6H_4OCH_3$, aryl.

According to yet another aspect of the invention, there is provided a protected, substituted γ-benzyl L-glutamate of formula 12:

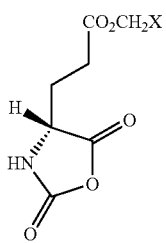

where X=$C_6H_5$, $C_6H_4Br$, $C_6H_4Cl$, $C_6H_4NO_2$ $C_6H_4OCH_3$, aryl.

According to yet another aspect of the invention, there is provided a substituted γ-benzyl L-glutamate of formula 12:

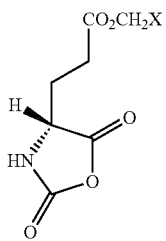

where X=$C_6H_5$, $C_6H_4Br$, $C_6H_4Cl$, $C_6H_4NO_2$ $C_6H_4OCH_3$, aryl.

According to yet another aspect of the invention, there is provided a substituted N$^\epsilon$-Benzyloxycarbonyl L-lysine of formula 11:

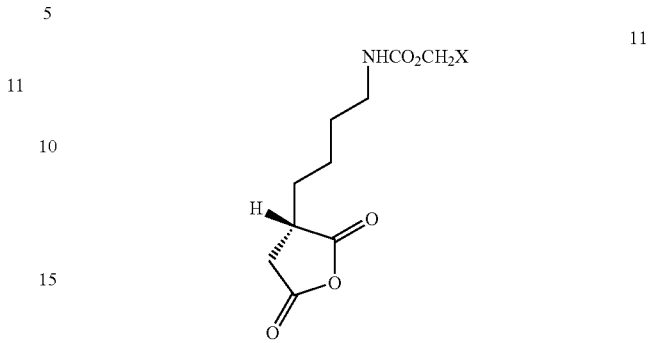

where X=$C_6H_5$, $C_6H_4Br$, $C_6H_4Cl$, $C_6H_4NO_2$ $C_6H_4OCH_3$, aryl.

According to yet another aspect of the invention, there is provided a substituted γ-benzyl L-glutamate of formula 12:

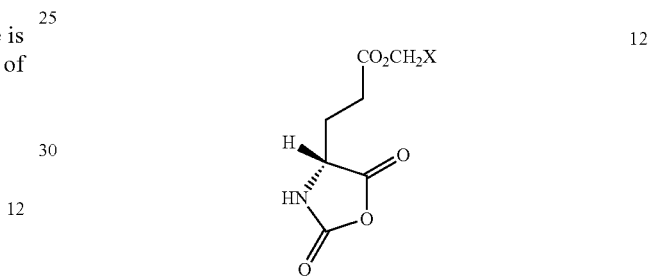

where X=$C_6H_5$, $C_6H_4Br$, $C_6H_4Cl$, $C_6H_4NO_2$ $C_6H_4OCH_3$, aryl.

According to yet another aspect of the invention, there is provided a substituted N$^\epsilon$-Benzyloxycarbonyl L-lysine of formula 11:

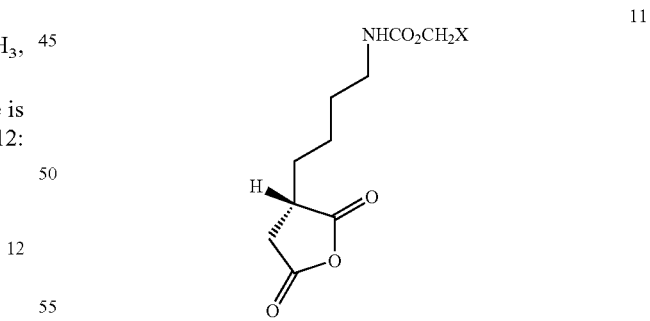

where X=$C_6H_5$, $C_6H_4Br$, $C_6H_4Cl$, $C_6H_4NO_2$ $C_6H_4OCH_3$, aryl.

According to yet another aspect of the invention, there is provided a protected copolymer 6 comprising a mixture of amino acids selected from the group consisting of L-alanine, L-tyrosine, L-glutamate and L-lysine, wherein said L-glutamate and L-lysine are protected by at least one protecting group, preferably said at least one protecting group is selected from a substituted or unsubstituted γ-benzyl group or a substituted or unsubstituted N$^\epsilon$-benzyloxycarbonyl group, or an aryl group, preferably said protected L-glutamate is as depicted below:

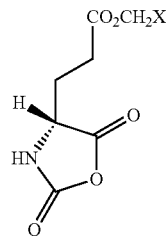

where X=$C_6H_5$, $C_6H_4Br$, $C_6H_4Cl$, $C_6H_4NO_2$ $C_6H_4OCH_3$, aryl.

and protected L-lysine is as depicted below:

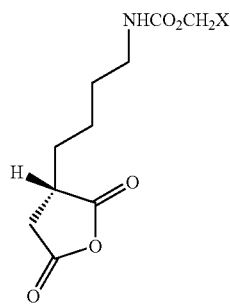

where X=$C_6H_5$, $C_6H_4Br$, $C_6H_4Cl$, $C_6H_4NO_2$ $C_6H_4OCH_3$, aryl.

Further and other objects of the invention will become apparent to a person reading the following.

DESCRIPTION OF THE INVENTION

In one embodiment of the present invention, polypeptide 1, comprising the following amino acid units in the structure, namely: L-alanine, L-glutamic acid, L-lysine and L-tyrosine randomly arranged in the polypeptide 1, is prepared by the polymerization of the N-carboxyanhydrides of L-alanine, tyrosine, γ-benzyl glutamate and $N^\epsilon$-benzyloxycarbonyl lysine, in various solvents. The four N-carboxyanhydrides are prepared starting from the corresponding commercially available benzyloxycarbonyl (Cbz) amino acids by using literature procedures.

In a preferred embodiment of the process according to the present invention, benzyl and benzyloxycarbonyl are preferably selected as a combination of protecting groups on glutamic acid and lysine, respectively, due to the facile cleavage of both by hydrogenation under hydrogen pressure or by catalytic transfer hydrogenation. This represents an elegant and simple procedure that can be executed without special equipment and resulting unexpectedly in a high yield in one instance a 70% yield, and facile performance thereof.

According to another preferred embodiment, the benzyl and benzyloxycarbonyl groups were substituted with at least one of the following: Br, Cl, $NO_2$, $OCH_3$, aryl.

In the present application, the term "room temperature" should be understood to mean a temperature ranging from about 20° C. to about 26° C.

The polymerization reaction of the four N-carboxyanhydrides may preferably be carried out in a solvent selected from the group comprising DMF, DMSO, $CH_2Cl_2$, dioxane or mixtures of these solvents, in one instance DMSO/DMF, DMF/$CH_2Cl_2$, dioxane/DMSO at temperatures ranging from about 0° C. to about 80° C. Preferably, the polymerization is carried out in the presence of an initiator which is selected from the group comprising: diethylamine, triethylamine and diisopropylamine (Scheme 4). In one instance, protected copolymer 6 was precipitated directly from the reaction mixture by addition of water.

Scheme 4

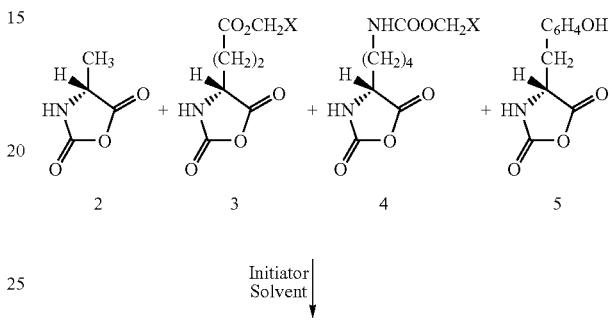

Initiator
Solvent

Protected Copolymer 6
where X = $C_6H_5$, $C_6H_4Br$, $C_6H_4Cl$, $C_6H_4NO_2$, $C_6H_4OCH_3$, aryl.

After polymerization, according to a preferred embodiment of the present invention, the deprotection step comprising the single-step removal of the γ-benzyl and $N^\epsilon$-benzyloxycarbonyl protecting groups present on protected copolymer 6 is carried out either by catalytic hydrogenation under high pressure (about 40 to about 100 psi) preferably at temperatures of about 50 to about 80° C. and more preferably in the presence of acetic acid, or by catalytic transfer hydrogenation (CTH), preferably in acetic acid and more preferably the catalysts are selected from the group consisting of Pd/C,. Pd(OH)$_2$, and the like, and also preferably at temperatures ranging from about 50° C. to about 80° C. (Scheme 5).

Scheme 5 protected copolymer 6

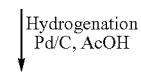
Hydrogenation
Pd/C, AcOH crude polypeptide 1
(as an acetate salt)

Preferably, the catalytic transfer hydrogenation incorporates various reagents, comprising 1,4-cyclohexadiene, cyclohexene, ammonium formate, formic acid, sodium formate, hydrazine, 1,3-cyclohexadiene, and trialkylammonium formates, or mixtures thereof. Catalytic transfer hydrogenation reagents such as these and others are well known in the prior art, and a selection can be made from these well-known reagents.

In one embodiment of the present invention, the resulting polypeptide 1 is isolated directly as an acetate salt after purification of the crude polypeptide 1 by a single dialysis step against water until the average molecular weight reaches the required value (Scheme 6).

Scheme 6 crude polypeptide 1
(as an acetate salt)

| Dialysis against water
↓

Polypeptide 1
(including Glatiramer Acetate)

In a preferred embodiment of the present invention, the average molecular weight of the polypeptide 1 is in the range of 4,700–11,000 Da. This value is representative for polypeptide 1 as well as Glatiramer acetate. The average molecular weight of the polypeptide was determined by Gel Permeation Chromatography.

In another preferred embodiment of the present invention, the polypeptide 1 is Glatiramer acetate and its preparation is performed as previously described in the present disclosure.

The following examples are purely illustrative of the invention and are not to be considered to limit the scope of the invention in any manner.

EXAMPLE 1

Preparation of Protected Copolymer 6

Alanine N-carboxyanhydride (10.08 g, 87.6 mmol), γ-Benzyl glutamate N-carboxyanhydride (7.04 g, 26.7 mmol), $N^\epsilon$-Benzyloxycarbonyl lysine N-carboxyanhydride (19.2 g, 62.7 mmol) and tyrosine N-carboxyanhydride (3.68 g, 17.7 mmol) were dissolved in dimethylformamide (160 mL) and treated with 0.9% wt. $Et_3N$. The reaction mixture was stirred for 24 hours at room temperature and under nitrogen and then poured into water (320 mL) and stirred for 6 hours. The product (protected copolymer 6: 27.39 g, 68%) was filtered, washed with water and dried.

EXAMPLE 2

Preparation of Protected Copolymer 6

Alanine N-carboxyanhydride (2.52 g, 2.19 mmol), γ-Benzyl glutamate N-carboxyanhydride (1.76 g, 6.6 mmol), $N^\epsilon$-Benzyloxycarbonyl lysine N-carboxyanhydride (4.8 g, 15.6 mmol) and tyrosine N-carboxyanhydride (0.92 g, 4.4 mmol) were dissolved in dimethylformamide (35.8 mL) and dichloromethane (15.4 ml) and treated with 0.9% wt. $Et_2NH$. The reaction mixture was stirred for 24 hours at room temperature and under nitrogen and then the dichloromethane was evaporated. The suspension was then poured into water (102 mL) and stirred for 6 hours. The product (protected copolymer 6: 7.35 g, 74%) was filtered, washed with water and dried.

EXAMPLE 3

Preparation of Polypeptide 1 by Catalytic Transfer Hydrogenation

Protected Copolymer 6 (2.00 g) was dissolved in 40 mL of acetic acid by heating at 80° C. under nitrogen. To the yellow solution was added 0.6 g Pd/C (30% wt.) and cyclohexene (5 mL) and then the reaction mixture was stirred at 80° C. under nitrogen for 4 hours. The reaction was filtered through celite and the cake was washed with 4 mL of hot acetic acid. After evaporation of the filtrate with 32 mL toluene, a beige solid was obtained (polypeptide 1, 1.4 g, 70%). The material obtained was dissolved in 28 ml of water, filtered through 2 g of celite and the clear solution was dialyzed against water in a dialysis bag for 24 h. Upon completion of the dialysis, the solution from the bag was evaporated to dryness by co-evaporation with toluene to yield polypeptide 1 as an off white solid.

EXAMPLE 4

Preparation of Polypeptide 1 by Catalytic Transfer Hydrogenation

Protected copolymer 6 (5.00 g) was dissolved in 100 mL of acetic acid by heating at 80° C. under nitrogen. To the yellow solution was added 1.5 g Pd/C (30% wt.) and 1,4-cyclohexadiene (7.4 mL) and then the reaction mixture was stirred at 80° C. under nitrogen for 48 hours. The reaction was filtered through celite and the cake washed with 20 mL of hot acetic acid. After evaporation of the filtrate with 32 mL toluene, a beige solid was obtained (polypeptide 1, 2.8 g, 56%). The material obtained was dissolved in 28 ml of water, filtered through 2 g of celite and the clear solution was dialyzed against water in a dialysis bag for 24 h. Upon completion of the dialysis, the solution from the bag was evaporated to dryness by co-evaporation with toluene to yield polypeptide 1 as an off white solid.

EXAMPLE 5

Preparation of Polypeptide 1 by Catalytic Transfer Hydrogenation

Protected copolymer 6 (1.00 g) was dissolved in 20 mL of acetic acid by heating at 80° C. under nitrogen. To the yellow solution was added 0.3 g Pd/C (30% wt.) and 1,4-cyclohexadiene (2.5 mL) and then the reaction mixture was stirred at 60° C. under nitrogen for 4 hours. The reaction was filtered through celite and the cake washed with 10 mL of hot acetic acid. After evaporation of the filtrate with 20 mL toluene, a beige solid was obtained (polypeptide 1, 0.54 g, 54%).

The material obtained by catalytic transfer hydrogenation may be purified by dialysis as previously described in Example 3.

EXAMPLE 6

Preparation of Polypeptide 1 by Catalytic Transfer Hydrogenation

Protected copolymer 6 (0.5 g) was dissolved in 10 mL of acetic acid by heating at 80° C. under nitrogen. To the yellow solution was added 0.15 g Pd/C (30% wt.) and ammonium formate (0.4 g) and then the reaction mixture was stirred at 70° C. under nitrogen for 24 hours. The reaction was filtered through celite and the cake washed with 10 mL of hot acetic acid. After evaporation of the filtrate with 20 mL toluene, the polypeptide 1 was obtained as a beige solid.

The material obtained by catalytic transfer hydrogenation may be purified by dialysis as previously described in Example 3.

EXAMPLE 7

Preparation of Polypeptide 1 by Hydrogenation

Protected copolymer 6 (2.00 g) was dissolved in 40 mL acetic acid by heating at 80° C. under nitrogen. The yellow solution was added 0.6 g Pd/C (30% wt.) and a hydrogen pressure of 80 psi was applied to the reaction mixture. After 10 h of stirring at 80° C. and 80 psi, the reaction was filtered through celite and the cake washed with 4 mL of hot acetic acid. After co-evaporation of the filtrate with 32 mL toluene, a beige solid was obtained (polypeptide 1, 1.4 g, 70%).

The material obtained by high pressure hydrogenation may be purified by dialysis as previously described in Example 3.

EXAMPLE 8

Preparation of Polypeptide 1 by Hydrogenation

Protected copolymer 6 (1.00 g) was dissolved in 20 mL acetic acid by heating at 80° C. under nitrogen. To the yellow solution was added 0.3 g Pd/C (30% wt.) and a hydrogen pressure of 60 psi was applied to the reaction mixture. After 10 h of stirring at 80° C. and 60 psi, the reaction was filtered through celite and the cake washed with 10 mL of hot acetic acid. After co-evaporation of the filtrate with 20 mL toluene, a beige solid was obtained (polypeptide 1, 0.6 g, 60%).

The material obtained by high pressure hydrogenation may be purified by dialysis as previously described in Example 3.

The invention claimed is:

1. A process for the preparation of polypeptide 1, or a pharmaceutically acceptable salt thereof, comprising L-alanine, L-glutamic acid, L-lysine and L-tyrosine randomly arranged in the polypeptide 1, wherein said process comprises the steps of:
   (a) polymerization of a mixture of the N-carboxyanhydrides of L-alanine, L-tyrosine, protected L-glutamate, and protected L-lysine, to obtain protected copolymer 6 or a salt thereof;
   (b) deprotection of the protected copolymer 6 or a salt thereof to afford polypeptide 1 or a pharmaceutically acceptable salt thereof in a single step;
   (c) separation and purification of the polypeptide 1 or a pharmaceutically acceptable salt thereof.

2. The process of claim 1, wherein said polymerization is carried out at a temperature ranging between about 0 to about 80° C.

3. The process of claim 2 wherein the polymerization is carried out in the presence of at least one solvent.

4. The process of claim 3 wherein said solvent is selected from the group consisting of DMF, DMSO, $CH_2Cl_2$, dioxane or mixtures thereof.

5. The process of claim 1, wherein said polymerization is carried out in the presence of an initiator.

6. The process of claim 5 wherein said initiator comprises at least one of the following: diethylamine, triethylamine and diisopropylamine.

7. The process of claim 1 wherein the deprotection step is selected from the group consisting of:
   (i) catalytic transfer hydrogenation; and
   (ii) catalytic hydrogenation under hydrogen pressure.

8. The process of claim 1, wherein said separation and purification of the polypeptide 1 is carried out in a single step.

9. The process of claim 8, wherein said single step involves is a single dialysis against water.

10. The process of claim 1, wherein said deprotection step is carried out in acetic acid.

11. The process of claim 10, wherein said deprotection step is carried out at a temperature in the range of about 50 to about 80° C.

12. The process of claim 11, wherein said deprotection step is carried out in the presence of a catalyst.

13. The process of claim 12, wherein said catalyst is selected from Pd/C and $Pd(OH)_2$.

14. The process of claim 7, wherein said catalytic transfer hydrogenation is carried out in the presence of acetic acid.

15. The process of claim 14, wherein said process is carried out at a temperature in the range of about 50 to about 80° C.

16. The process of claim 14, wherein the catalyst is selected from Pd/C and $Pd(OH)_2$, and said process is carried out in the presence of at least one reagent selected from the group consisting of: formic acid, sodium formate, trialkyl ammonium formates, hydrazine, 1,3-cyclohexadiene, 1,4-cyclohexadiene, cyclohexene, and ammonium formate or mixtures thereof.

17. The process of claim 1, wherein said deprotection step is carried out at a pressure in the range of about 40 to about 100 psi.

18. The process of claim 7 wherein said catalytic hydrogenation is carried out under hydrogen pressure of about 40 to about 100 psi.

19. The process of claim 7 wherein said catalytic hydrogenation is carried out under hydrogen pressure of about 40 to about 100 psi at a temperature in the range of about 50 to about 80° C.

20. The process of claim 7 wherein said catalytic hydrogenation is carried out under hydrogen pressure of about 40 to about 100 psi in the presence of acetic acid and at a temperature in the range of about 50 to about 80° C.

21. A process of manufacturing Glatiramer Acetate comprising a single step deprotection of a protected copolymer 6, said protected copolymer 6 comprising a mixture of L-alanine, L-tyrosine, protected L-glutamate and protected L-lysine randomly arranged in the copolymer 6, and, wherein said protected L-glutamate and protected L-lysine are protected by at least one protecting group.

22. The process as claimed in claim 21, wherein said at least one protecting group is selected from a substituted or unsubstituted γ-benzyl group or a substituted or unsubstituted $N^\epsilon$-benzyloxycarbonyl group or an aryl group.

23. The process as claimed in claim 22, wherein said substituted γ-benzyl group or $N^\epsilon$-benzyloxycarbonyl group is substituted with at least one of the following: Br, Cl, $NO_2$, $OCH_3$.

24. The process of claim 21, wherein the deprotection step is selected from the group consisting of:
   (i) catalytic transfer hydrogenation; and
   (ii) catalytic hydrogenation under hydrogen pressure.

25. The process of claim 21, wherein said deprotection step is carried out in acetic acid.

26. The process of claim 25, wherein said deprotection step is carried out at a temperature of about 50 to about 80° C.

27. The process of claim 26, wherein said deprotection step is carried out in the presence of a catalyst selected from Pd/C and $Pd(OH)_2$.

28. The process of claim 27, wherein said deprotection step further comprises is carried out in the presence of at least one reagent selected from the group consisting of: formic acid, sodium formate, trialkyl ammonium formates, hydrazine, 1,3-cyclohexadiene, 1,4-cyclohexadiene, cyclohexene, and ammonium formate, or mixtures thereof.

29. The process of claim 21, wherein said deprotection step is carried out at a pressure in the range of about 40 to about 100 psi.

30. The process of claim 24, wherein said catalytic hydrogenation is carried out under hydrogen pressure of about 40 to about 100 psi.

31. The process of claim 24, wherein said catalytic hydrogenation is carried out under hydrogen pressure of about 40 to about 100 psi at a temperature in the range of about 50 to about 80° C.

32. The process of claim 24, wherein said catalytic hydrogenation is carried out under hydrogen pressure of about 40 to about 100 psi in the presence of acetic acid and at a temperature in the range of about 50 to about 80° C.

33. The process of claim 21 further comprising subsequent separation and purification of Glatiramer Acetate.

34. The process of claim 33, wherein said separation and purification of the Glatiramer Acetate is carried out in a single step.

35. The process of claim 34, wherein said single step a single dialysis against water.

36. The process according to claim 1, wherein the Polypeptide 1 has an average molecular weight between 4,700 and 11,000 Da.

37. The process according to claim 21, wherein Glatiramer Acetate has an average molecular weight between 4,700 and 11,000 Da.

38. The process of claim 1, wherein the N-carboxyanhydride of protected L-glutamate is a substituted

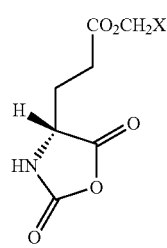

12 where $X=C_6H_5$, $C_6H_4Br$, $C_6H_4Cl$, $C_6H_4NO_2$ $C_6H_4OCH_3$ or aryl.

39. The process of claims 1 or 21, wherein the protected L-lysine is a substituted $N^\epsilon$-Benzyloxycarbonyl L-lysine of formula 11:

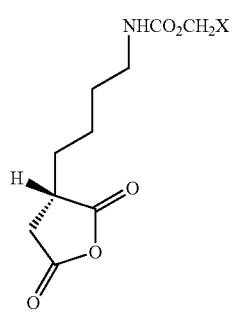

11 where $X=C_6H_5$, $C_6H_4Br$, $C_6H_4Cl$, $C_6H_4NO_2$ $C_6H_4OCH_3$ or aryl.

40. Protected copolymer 6 or a pharmaceutically acceptable salt thereof, comprising L-alanine, L-tyrosine, protected L-glutamate, and protected L-lysine randomly arranged in the copolymer 6, prepared according to a process comprising the step:

(a) polymerization of a mixture of the N-carboxyanhydrides of L-alanine, L-tyrosine, protected L-glutamate, and protected L-lysine, to obtain protected copolymer 6 or a pharmaceutically acceptable salt thereof, wherein the N-carboxyanhydride of protected L-glutamate is:

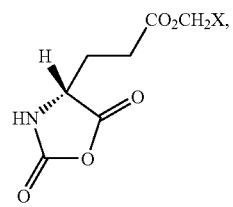

where X is $C_6H_4Br$, $C_6H_4Cl$, $C_6H_4NO_2$, $C_6H_4OCH_3$, or aryl, with the proviso that aryl is not $C_6H_5$.

41. Protected copolymer 6 or a pharmaceutically acceptable salt thereof, comprising L-alanine, L-tyrosine, protected L-glutamate, and protected L-lysine randomly arranged in the copolymer 6, prepared according to a process comprising the step:

(a) polymerization of a mixture of the N-carboxyanhydrides of L-alanine, L-tyrosine, protected L-glutamate, and protected L-lysine, to obtain protected copolymer 6 or a pharmaceutically acceptable salt thereof, wherein the N-carboxyanhydride of protected L-lysine is:

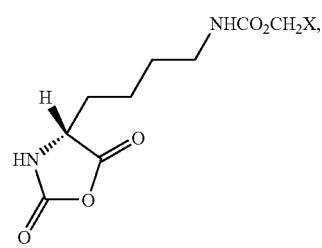

where X is $C_6H_5$, $C_6H_4Br$, $C_6H_4Cl$, $C_6H_4NO_2$, $C_6H_4OCH_3$, or aryl.

42. Protected copolymer 6 or a pharmaceutically acceptable salt thereof, comprising L-alanine, L-tyrosine, protected L-glutamate, and protected L-lysine randomly arranged in the copolymer 6, prepared according to a process comprising the step:

(a) polymerization of a mixture of the N-carboxyanhydrides of L-alanine, L-tyrosine, protected L-glutamate, and protected L-lysine, to obtain protected copolymer 6 or a pharmaceutically acceptable salt thereof, wherein the N-carboxyanhydride of protected L-lysine is:

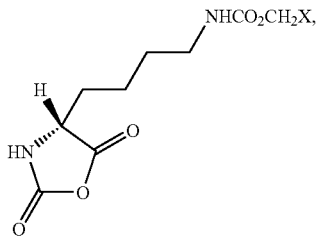

where X is $C_6H_5$, $C_6H_4Br$, $C_6H_4Cl$, $C_6H_4NO_2$, $C_6H_4OCH_3$, or aryl; and the N-carboxyanhydride of protected L-glutamate is:

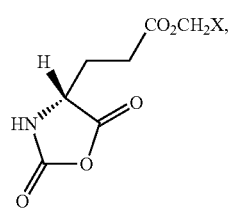

where X is $C_6H_5$, $C_6H_4Br$, $C_6H_4Cl$, $C_6H_4NO_2$, $C_6H_4OCH_3$, or aryl.

43. Protected copolymer 6 or a pharmaceutically acceptable salt thereof, comprising L-alanine, L-tyrosine, protected L-glutamate, and protected L-lysine randomly arranged in the copolymer 6, wherein the protected L-lysine is:

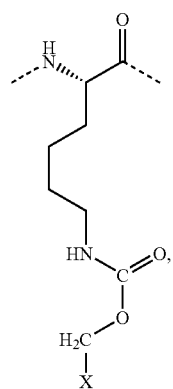

where X is $C_6H_5$, $C_6H_4Br$, $C_6H_4Cl$, $C_6H_4NO_2$, $C_6H_4OCH_3$, or aryl.

44. Protected copolymer 6 or a pharmaceutically acceptable salt thereof, comprising L-alanine, L-tyrosine, protected L-glutamate, and protected L-lysine randomly arranged in the copolymer 6, wherein the protected L-glutamate is:

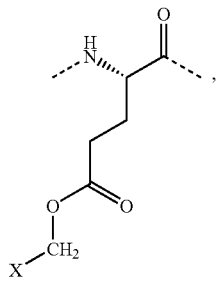

wherein X is $C_6H_4Br$, $C_6H_4Cl$, $C_6H_4NO_2$, $C_6H_4OCH_3$, or aryl, with the proviso that aryl is not $C_6H_5$.

45. Protected copolymer 6 or a pharmaceutically acceptable salt thereof, comprising L-alanine, L-tyrosine, protected L-glutamate, and protected L-lysine randomly arranged in the copolymer 6, wherein the protected L-lysine is:

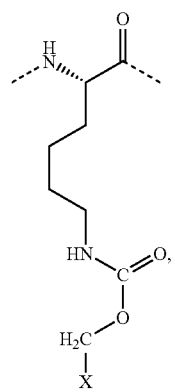

where X is $C_6H_5$, $C_6H_4Br$, $C_6H_4Cl$, $C_6H_4NO_2$, $C_6H_4OCH_3$, or aryl; and
the protected L-glutamate is:

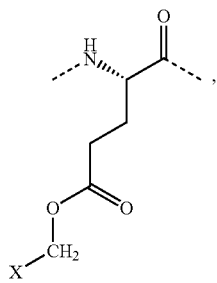

wherein X is $C_6H_5$, $C_6H_4Br$, $C_6H_4Cl$, $C_6H_4NO_2$, $C_6H_4OCH_3$, or aryl.

* * * * *